United States Patent
Ramathal et al.

(10) Patent No.: US 10,298,405 B2
(45) Date of Patent: *May 21, 2019

(54) HARDWARE BLOCKCHAIN CONSENSUS OPERATING PROCEDURE ENFORCEMENT

(71) Applicant: Accenture Global Solutions Limited, Dublin (IE)

(72) Inventors: Noel Vivek Ramathal, Chicago, IL (US); Kevin Bernard Greene, Miami Beach, FL (US)

(73) Assignee: Accenture Global Solutions Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/000,028

(22) Filed: Jun. 5, 2018

(65) Prior Publication Data
US 2018/0287805 A1    Oct. 4, 2018

Related U.S. Application Data

(63) Continuation of application No. 15/595,537, filed on May 15, 2017, now Pat. No. 9,998,286.
(Continued)

(51) Int. Cl.
*H04L 9/32* (2006.01)
*G06Q 50/24* (2012.01)
(Continued)

(52) U.S. Cl.
CPC .......... *H04L 9/3268* (2013.01); *G06F 21/33* (2013.01); *G06F 21/6245* (2013.01);
(Continued)

(58) Field of Classification Search
CPC .......................... H04L 9/3268; H04L 9/3265
(Continued)

(56) References Cited

U.S. PATENT DOCUMENTS 5,586,313 A    12/1996  Schnittker et al.
7,590,669 B2*  9/2009   Yip ..................... H04L 41/0816
(Continued)

FOREIGN PATENT DOCUMENTS

CN      106097006        11/2016
WO    WO 2016/015041 A1   1/2016
(Continued)

OTHER PUBLICATIONS

Ateniese, G., et al. *"Redactable Blockchain, or Rewriting History in Bitcoin and Friends,"* Cryptology ePrint Archive: Report 2016/757, Aug. 5, 2016 (36p).
(Continued)

*Primary Examiner* — Dant B Shaifer Harriman
(74) *Attorney, Agent, or Firm* — Brinks Gilson & Lione

(57) ABSTRACT

A system may provide hardware acceleration for corrective blockchain-based record entry. Blockchain management circuitry (BMC) may receive a correction to a record entry. The BMC may access a consensus operating procedure. The BMC may apply the consensus operating procedure to the record entry to determine a corrective indicator. After completing the consensus operating procedure, the BMC may append a corrective block generated based on the record entry and corrective indicator to the blockchain. Accordingly, the system may ensure that corrective blocks added to the blockchain were generated in compliance with the consensus operating procedure.

20 Claims, 12 Drawing Sheets

Related U.S. Application Data

(60) Provisional application No. 62/460,355, filed on Feb. 17, 2017.

(51) Int. Cl.

| | | |
|---|---|---|
| *G06F 21/33* | (2013.01) | |
| *H04L 29/06* | (2006.01) | |
| *G16H 10/60* | (2018.01) | |
| *G06Q 10/10* | (2012.01) | |
| *G06Q 20/02* | (2012.01) | |
| *G16H 15/00* | (2018.01) | |
| *G06F 21/62* | (2013.01) | |

(52) U.S. Cl.
CPC ............ *G06Q 10/10* (2013.01); *G06Q 20/02* (2013.01); *G06Q 50/24* (2013.01); *G16H 10/60* (2018.01); *G16H 15/00* (2018.01); *H04L 9/3239* (2013.01); *H04L 63/102* (2013.01); *H04L 63/0823* (2013.01); *H04L 2209/38* (2013.01)

(58) Field of Classification Search
USPC ......................................................... 713/156
See application file for complete search history.

(56) References Cited

U.S. PATENT DOCUMENTS

| | | | | |
|---|---|---|---|---|
| 8,073,777 | B2 * | 12/2011 | Barry ................. | G06F 11/0709 705/50 |
| 9,679,276 | B1 | 6/2017 | Cuende | |
| 9,825,931 | B2 | 11/2017 | Johnsrud et al. | |
| 9,998,286 | B1 | 6/2018 | Ramathal et al. | |
| 2008/0091981 | A1 * | 4/2008 | Dokken ......... | G01R 31/318533 714/45 |
| 2012/0005192 | A1 | 1/2012 | Bao | |
| 2012/0110445 | A1 | 5/2012 | Greenspan et al. | |
| 2015/0205929 | A1 | 7/2015 | Brama | |
| 2015/0269570 | A1 | 9/2015 | Phan et al. | |
| 2015/0332283 | A1 | 11/2015 | Witchey | |
| 2015/0379510 | A1 | 12/2015 | Smith | |
| 2016/0027229 | A1 | 1/2016 | Spanos et al. | |
| 2016/0191243 | A1 | 6/2016 | Manning | |
| 2016/0253622 | A1 | 9/2016 | Sriram | |
| 2016/0275461 | A1 | 9/2016 | Sprague et al. | |
| 2016/0330027 | A1 | 11/2016 | Ebrahimi | |
| 2016/0358135 | A1 | 12/2016 | Liao et al. | |
| 2016/0379212 | A1 | 12/2016 | Bowman | |
| 2017/0039330 | A1 | 2/2017 | Tanner, Jr. et al. | |
| 2017/0046669 | A1 | 2/2017 | Chow | |
| 2017/0053293 | A1 | 2/2017 | Choi | |
| 2017/0076280 | A1 | 3/2017 | Castinado et al. | |
| 2017/0091397 | A1 | 3/2017 | Shah | |
| 2017/0149819 | A1 | 5/2017 | Androulaki et al. | |
| 2017/0163733 | A1 | 6/2017 | Grefen et al. | |
| 2017/0178072 | A1 | 6/2017 | Poornachandran | |
| 2017/0213209 | A1 | 7/2017 | Dillenberger | |
| 2017/0228371 | A1 | 8/2017 | Seger, II | |
| 2017/0228734 | A1 | 8/2017 | Kurian | |
| 2017/0232300 | A1 | 8/2017 | Tran | |
| 2017/0236123 | A1 * | 8/2017 | Ali ....................... | G06Q 20/401 705/75 |
| 2017/0374049 | A1 * | 12/2017 | Ateniese ............... | G06F 3/0619 |
| 2018/0225175 | A1 | 8/2018 | Tomlinson et al. | |
| 2018/0323980 | A1 | 11/2018 | Ahn et al. | |
| 2019/0018984 | A1 | 1/2019 | Setty et al. | |

FOREIGN PATENT DOCUMENTS

| | | |
|---|---|---|
| WO | WO 2017/004527 A1 | 1/2017 |
| WO | WO 2017/202759 A1 | 11/2017 |

OTHER PUBLICATIONS

Australian Patent Office Examination Report No. 1 for Australia Patent Application No. 2017204196 dated Nov. 14, 2017, 8 pages.
Australian Patent Office Examination Report No. 1 for Australian Application No. 2017204199 dated Oct. 19, 2017, 5p.
Australian Patent Office Examination Report No. 2 for Australian Patent Application No. 2017204199 dated Mar. 8, 2018, pp. 1-4.
Broderson, C., et al., Blockchain: Securing a New Health Interoperability Experience, Aug. 2016, pp. 1-11, Accenture, Chicago, Illinois.
Final Office Action for U.S. Appl. No. 15/595,597, dated Feb. 1, 2018, 34 pages.
Non-Final Office Action for U.S. Appl. No. 15/595,597, dated Aug. 23, 2017, 31 pages.
European Patent Office, Extended European Search Report for European application No. 17177502.6, dated Nov. 20, 2017, 6 pages.
European Patent Office, Extended European Search Report from European Patent Application No. 17177509.1 dated Feb. 7, 2018 pp. 1-6.
Hardjono, T. et al., 'Anonymous Identities for Permissioned Blockchains,' Jan. 20, 2016, Viewed on the Internet on Nov. 14, 2017, retrieved on Nov. 14, 2017 from the Internet <URL: http://connection.mit.edu/wp-content/uploads/sites/29/2014/12/Anonymous-Identities-for-Permissioned-Blockchains2.pdf>.
Healthcare rallies for blockchains, IBM Institute for Business Value survey conducted by The Economist Intelligence Unit, Dec. 2016, pp. 1-22, IBM Corporation, Somers, New York.
Puddu, I., et al., "μchain: How to Forget Without Hard Forks,"Cryptology ePrint Archive: Report 2017/106, Feb. 14, 2017, (23p).
Sanson, T., 'Consensus-as-a-service: a brief report on the emergence of permissioned, distributed ledger systems,' Apr. 6, 2015, Viewed on the Internet on Nov. 14, 2017, retrieved on Nov. 14 from the Internet <URL: https://pdfs.semanticscholar.org/f3a2/2daa64fc82fcda47e86ac50d555ffc24b8c7.pdf>.
Sheppard, M. D., 'Implementing the Central Bank Functionality of RSCoin, a Centrally Banked Cryptocurrency,'193 MSC Thesis, University College London, Aug. 26, 2016, Viewed on the Internet on Nov. 14, 2017, retrieved on Nov. 14 from the Internet <URL: https://iamjustatad.files.wordpress.com/2016/11/rscoin_thesis.pdf>.
Swan, "Blockchain: Blueprint for a New Economy" in "Blockchain: Blueprint for a New Economy" dated Feb. 8, 2015, pp. 59 and 61.
Australian Patent Office, Examination Report No. 2 in Australian Application No. 2017204196, dated May 3, 2018, pp. 1-7.
Narayanan, et al., "Bitcoin and Cryptocurrency Technologies: A Comprehensive Introduction" Princeton University Press, Princeton, New Jersey, dated Jan. 1, 2016, 41 pages.
Non-Final Office Action in U.S. Appl. No. 15/595,597 dated Jun. 11, 2018, 34 pages.
Examination Report No. 3 for Australia Application No. 2017204199, dated Aug. 6, 2018, pp. 1-7.
Examination Report No. 4 for Australia application No. 2017204199, dated Oct. 16, 2018, pp. 1-5.
Bitcoin, Wikipedia captured Feb. 16, 2017 and obtained from the Internet on Dec. 7, 2018, from URL: <https://web.archive.org/web/20170216044527/https://en.wikipedia.org/wiki/Bitcoin>, pp. 1-41.
Examination Report No. 3 for Australia application No. 2017204196, dated Oct. 18, 2018, pp. 1-7.
Office Action in U.S. Appl. No. 15/595,597, dated Jan. 4, 2019, pp. 1-44.

\* cited by examiner

HARDWARE BLOCKCHAIN CONSENSUS OPERATING PROCEDURE ENFORCEMENT

PRIORITY CLAIM

This application is a continuation of and claims priority to U.S. application Ser. No. 15/595,537, filed 15 May 2017, titled "Hardware Blockchain Consensus Operating Procedure Enforcement," which is incorporated by reference in its entirety. U.S. application Ser. No. 15/595,537 claims the benefit of U.S. Provisional Patent Application Ser. No. 62/460,355, filed 17 Feb. 2017, and titled "Hardware Blockchain Health Processing Acceleration."

CROSS-REFERENCE TO RELATED APPLICATIONS

This application is related to U.S. patent application Ser. No. 15/595,597, filed on 15 May 2017, titled "Hardware Blockchain Corrective Consensus Operating Procedure Enforcement," which is incorporated by reference in its entirety.

TECHNICAL FIELD

This disclosure relates to computer hardware acceleration of blockchain-based multi-party processes.

BACKGROUND

Rapid advances in electronics and communication technologies, driven by immense customer demand, have resulted in newly emerging complex network transaction chains. Improvements in the hardware and software implementations of the underlying processing for the transaction chains will increase the security, reliability, and speed of the implementations.

DETAILED DESCRIPTION

Figure 1:
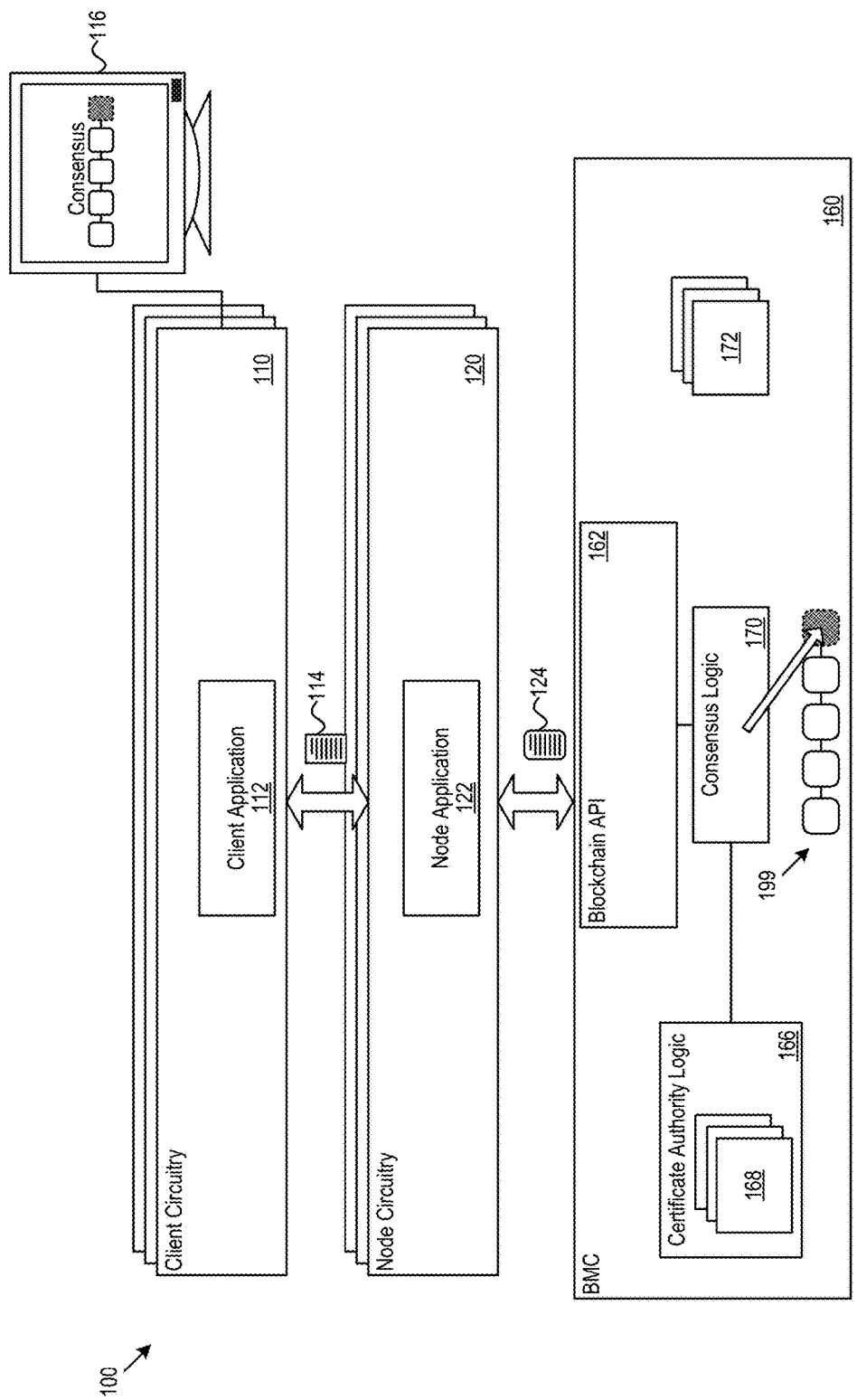
FIG. 1 shows an example accelerated record entry hardware system.

When multiple nodes coordinate to place entries in a record, the parties represented by the multiple nodes may be dependent on other nodes following the consensus operating procedure or terms when creating entries in the record. For example, a consensus operating procedure may include a procedure enforced through a blockchain consensus mechanism. Situations in which a node posts an entry to the record without first following the consensus operating procedure may necessitate corrections that ripple through multiple ledger entries and consume hardware processing resources. The techniques and architectures described below help ensure that nodes execute the consensus operating procedure before creating a ledger entry, thereby improving the operation of the underlying hardware, e.g., by reducing the overall processing load, eliminating errors, and reducing overall resource expenditure for achieving correct records. Further, the techniques and architectures will increase the overall real-time accuracy of the entries produced as a result of the hardware processing. Accordingly, the techniques and architectures provide technical solutions resulting in technical improvements to existing options data transaction systems.

In an example real-world processing scenario, multiple nodes operated on behalf of multiple parties in a health claim system may make entries to a health accum ledger. A health accum may include one or more tracked values that accumulate over time, such as deductible contributions or out-of-pocket contributions. The multiple parties may agree in advance to a consensus operating procedure for posting an entry to the ledger. For example, as discussed in detail below, the consensus process may include: a) performing memory access operations at one more memory locations within a blockchain, e.g., a blockchain storing recorded data, to obtain a previous accum value; b) applying one or more processor-level operations, such as "add" or "mult" operations or other processor-level operations, on the accum value to update the previous accum value to a current accum value; and c) performing additional processor-level add or mult processing operations on other accum values in the blockchain to reconcile other entries with the current accum value. Ensuring that each of the nodes placing entries in the health accum follows the consensus operating procedure reduces the overall processing resources consumed by increasing the probability of compliance by the different nodes. In other contexts, the system may be used to track usage, contributions, or other accumulated values. For example, the system may be used to track data plan usage in cellular phone contract contexts, or other accumulated values. For example, accumulated values may include values that are tracked by the system over time and tally the value of one or more related operations or transactions.

In some implementations, compliance with the consensus operating procedure among the nodes may be enforced through a blockchain consensus mechanism. The consensus operation procedure may be codified by the system into the terms of a smart contract. For example, the parties may determine the consensus operating procedure ahead of performing governed transactions and then codify the consensus operating procedure into a smart contract. Enforcing a consensus operating procedure may ensure consistency and accuracy among record entries, which may increase the reliability of the system.

When a node follows the consensus operating procedure during posting of an entry, e.g., by complying with the terms of the smart contract, the system may provide a validity indicator for the entry created. The validity indicator may be stored or otherwise associated with the blockchain such that parties later reviewing the blockchain may confirm that the node followed the consensus operating procedure while posting the entry. Additionally or alternatively, the system may withhold the validity indicator (or provide an invalidity indicator) when a node deviates from the consensus operating procedure when posting an entry. Validity indicators may include proof of work, hashes, security tokens, security certificates, or other indicators of compliance.

Additionally or alternatively, the system may enforce smart contract terms through verification of procedure adherence. For example, a smart contract may define a consensus operation procedure. After a block is added to the blockchain under the direction of a node, the added block may be reviewed for compliance to determine if the block is valid. If the system added the block without properly following the defined consensus procedure, the block may be ignored. In some cases, the block may not necessarily include an indicator of validity or invalidity, rather validity (invalidity) may be inferred by the system by reviewing the contents of the block to determine if the system followed the consensus operating procedure.

Additionally or alternatively, the techniques and architectures described herein may be used to increase the security of the underlying hardware processing system. For example, security may be increased by integrating security rules into the consensus operating procedure. In an example, scenario a health accum processing node may be barred by the security rules from viewing portions of the blockchain. If the health accum processing node accesses (or attempts to accesses) a portion of the blockchain without authorization, the node may deviate from the consensus operating procedure. Accordingly, a future entry made by node may be invalidated responsive to the deviation from the consensus operating procedure. In various implementations, the invalidations may apply to the next entry made by the node, all future entries, entries for a predetermined duration after the deviation, entries related contextually to the unauthorized access, or other set of entries.

FIG. 1 shows an example accelerated record entry hardware system 100 ("system 100"). The system 100 may include client circuitry 110, node circuitry 120, and blockchain management circuitry (BMC) 160. The client circuitry 110, node circuitry 120, and BMC 160 may be implemented in various configurations including distributed deployments and/or logically-separated deployments on physically-unified systems. In some implementations, the hardware configuration of any combination of the client circuitry 110, node circuitry 120, BMC 160 or any portions thereof may be specified via a deployment manifest. The deployment manifest may be used to requisition hardware computing resources to serve as a platform for the designated configuration in the manifest.

The client circuitry 110 may execute a record entry client application 112. The record entry client application 112 may capture record entry information 114 from data input sources for example, scanned records, man-machine interface devices, connected devices (e.g., internet of things (IoT) medical devices or other IoT devices), or other input sources. The client circuitry 110 may package the record entry information 114 for provision to the node circuitry 120. For example, the client circuitry 110 may send the record entry information 114 to the node circuitry 120 as a packet with fields designated for the various record entry information types (e.g., transaction IDs, claim amounts, service dates, submission dates, or other entry information types). In some cases, the client circuitry may format the record entry information 114 for delivery via an electronic form, such as a web form, provided by the node circuitry 120. The record entry information 114 may be formatted for the forms automatically, e.g., after capture from a document scan, manually, or any combination thereof.

The client circuitry 110 may be coupled to a display 116. The display 116 may display interfaces for input of record entry information. Additionally or alternatively, the client application may generate presentations of previous record entry information obtained from the blockchain. For example, the client application 112 may generate the presentations from data stored on previous block of the blockchain. The node circuitry 120 may provide the data from the blockchain after receiving the data from the BMC 160.

The node circuitry 120 may receive the record entry information through a node application 122. For example, the node application 122 may host an electronic form to facilitate reception of the record entry information, parse a received packet containing the record entry information, or perform other information reception tasks. The node application 122 may process the record entry information and generate a record entry 124 for the blockchain 199. For example, in the health claim processing scenario, the record entry may comprise a claim for entry into a ledger system stored on the blockchain 199.

In some implementations, the system 100 may implement multiple instances of node circuitry 120. The system 100 may group node circuitry 120 usage according to one or more criteria. For example, the system 100 may group node circuitry 120 usage according to enterprise or claim-type association. For example, medical claim providing parties may operate on node circuitry 120 separate from parties providing pharmaceutical claims, dental claims, vision claims, mental health claims, or other healthcare types. Additionally or alternatively, the system 100 may group parties subject to different consensus operating procedures on different node circuitry. In some cases, usage may be dynamically assigned by the system 100. For example, node circuitry usage may depend on the content of the record entry information 114. For example, a party may connect to first node circuitry when submitting a claim of a first type. However, that same party might connect to second, different node circuitry when submitting another claim of a second type different from the first. Additionally or alternatively, dynamic node circuitry 120 usage allotments may be assigned based on processing and load-balancing concerns.

The node application 122 may be in data communication with a blockchain application programming interface (API) 162 running on the BMC 160. The blockchain API 162 may provide access to blockchain storage options for the record entry.

The blockchain API 162 may access a certificate authority logic 166 running on the BMC 160. The certificate authority logic 166 may issue certificates 168 used to manage access to various portions of the blockchain 199. The individual certificates may assigned according to node. Additionally or alternatively, if multiple parties use a common node, certificates may be assigned according to party affiliation. Thus, the system 100 may use the certificates 168 to verify the nodes (and/or parties) do not access portions of the blockchain 199 for which they lack authorization.

Figure 2:
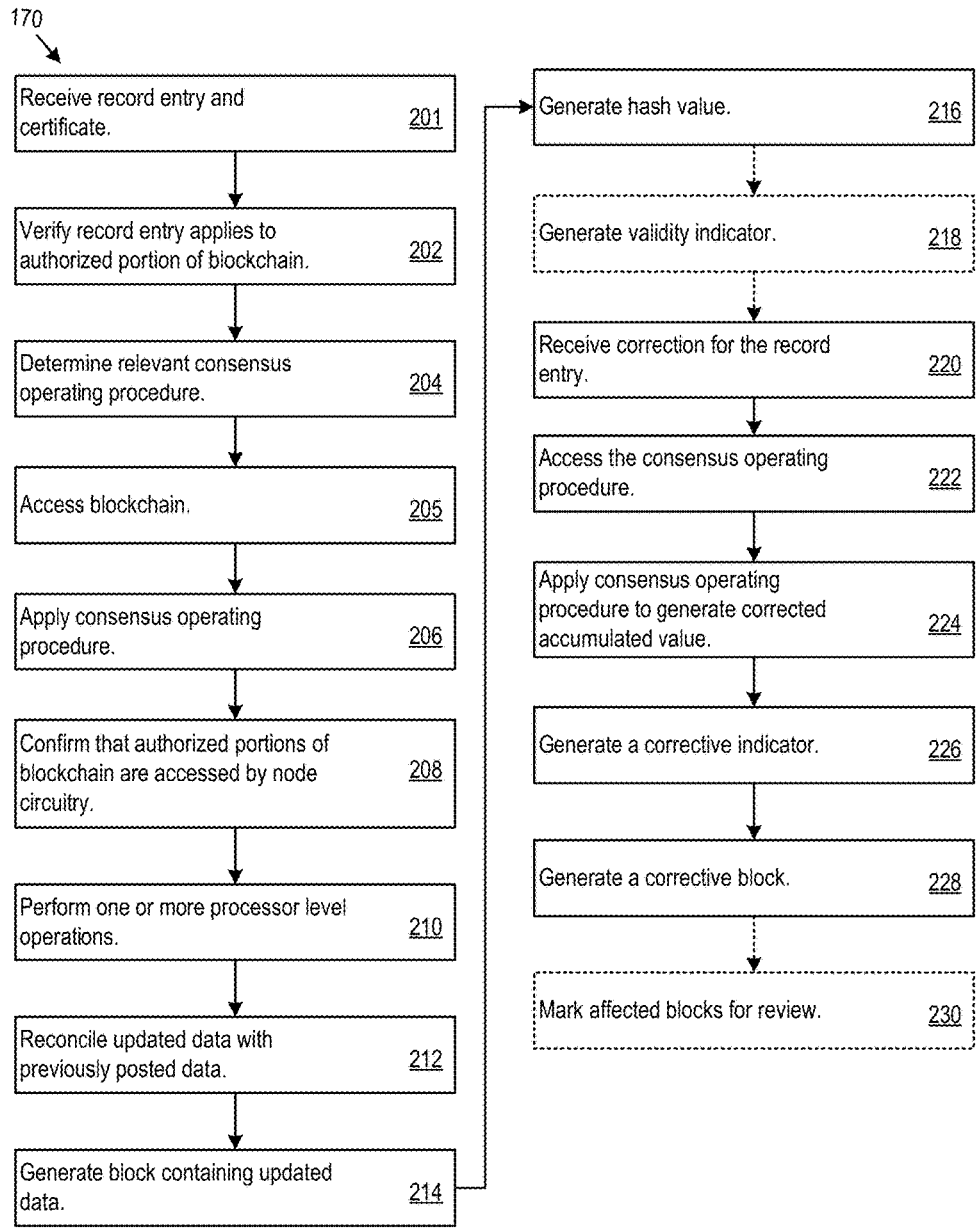
FIG. 2 shows example consensus logic.

While continuing to refer to FIG. 1, the discussion also makes reference to FIG. 2, which shows example processing logic that the consensus logic 170 may implement. The logical features of consensus logic 170 may be implemented in various orders and combinations. For example, in a first implementation, one or more features may be omitted or reordered with respect to a second implementation. The consensus logic 170 may be executed on the on the BMC 160. The blockchain API may receive the record entry and a certificate 168 (201). When the blockchain API 162 receives the record entry 124 and the certificate 168, the consensus logic 170 may verify that the record entry 124 applies to a portion of the blockchain 199 that the node circuitry 120 or party that sent the record entry 124 has access (202). The consensus logic 170 may determine the relevant consensus operating procedure response to the node, the party that initiated the record entry, the type of accumulated value affected by the transaction, the certificate 168, or a combination thereof (204). The consensus logic 170 may access the blockchain 199 (205). The consensus logic 170 may apply the consensus operating procedure to the record entry 124 (206). The consensus operating procedure may be codified in consensus operation procedure definitions 172 (e.g., smart contract terms), which may be managed by consensus logic 170. For example, the consensus operating procedure may include using the certificate to confirm that authorized portions of the blockchain 162 are accessed by the node circuitry through the blockchain API 162 while the blockchain API 162 is in data communication with the node circuitry 120 (208).

Additionally or alternatively, the consensus logic 170 may perform one or more processor-level operations to perform on data in the record entry 124 and blockchain 162 to generate updated data (210). For example, as discussed above, processor-level operations may include add operations, mult operations, or other processor-level operations. Based on the updated data, the consensus logic 170 may reconcile the updated data with previously posted data from the blockchain 199 (212). For example, the blockchain 199 may include earlier accumulated values that are affected by the new data provided. For example, the updated data may include a correction to a past accumulated value stored in the blockchain 199. The correction may affect transactions occurring after the correction that may have already been added to the blockchain 199 by the system 100. When the consensus logic 170 completes the consensus operating procedure, the consensus logic 170 may generate a block containing the updated data (214).

The consensus logic may generate a hash value for a preceding block and place the hash value in the block along with the updated data to form a link between the block on the blockchain (216). The hash value may create a blockchain link in the blockchain. In other words, the hash value may generate a verifiable record of the content of the preceding block. Accordingly, the preceding block may not be changed without creating evidence of tamper. In various implementations, the block may include multiple fields including a payload field and a hash field. The record entry may be placed in the payload field, while the generated hash value may be placed in the hash field. The hash value may be generated using a cryptographic hash function, a cyclic redundancy check, or other checksum function.

In various implementations, multiple record entries (e.g., covering multiple transactions) may be reflected in the payload of a single block. Allowing multiple record entries to be reflected in the payload of a single block may allow for compactness in blockchain storage because a smaller number of total blocks would be needed to cover multiple record entries compared with systems representing only a single record entry in a single block.

In some implementations, a single block may store a single record entry. Such storage constraints may allow for a clearer relationship between blocks and record entries. Accordingly, in a single block/single record entry implementation, reference to a particular block unambiguously refers to the corresponding record entry. Accordingly, referencing past record entries may be have data access efficiency gains by such a storage system.

In some cases where a record entry may be large or complex, e.g., by including detailed description notes or media attachments, the record entry may be stored across multiple blocks.

In some cases where validity indicators are used, the consensus logic 170 may generate a validity indicator and place the indicator in the block along with the updated data and hash value (218).

In some implementations, after a block has been generated and added to the blockchain, the BMC 160 may receive a correction for the record entry on which the updated data was based (220). For example, a correction may arise from a change to the underlying record entry information 114 (e.g., a change to identification information, amounts, dates, or other record entry information), a change to the applicable consensus operating procedure that results in a change to the record entry (e.g., an error may be discovered in the procedure, an accum value threshold may be adjusted, the incorrect consensus operating procedure may have been previously applied, or other correction), or both. Accordingly, the consensus logic 170 may operate to apply the correction to the previously formed block in the blockchain 199.

The consensus logic 170 may access the consensus operating procedure definitions 172 (222) or an identifier for the consensus operating procedure to call or execute. The consensus logic 170 may apply the consensus operating procedure to generate a corrected accumulated value from the previous accumulated value stored in the previously formed block (224). Based on the corrected accumulated value, the correction and the previously formed block, the consensus logic 170 may generate a corrective indicator that references the previously formed block and includes the corrected accumulated value, data from the correction, or both (226).

The consensus logic 170 may generate a corrective block that includes the corrective indicator and a hash value generated using the content of a block preceding the corrective block (228). In some cases, the preceding block may be the same block as the previously formed block. However, in other cases, intervening blocks may be present between the previously formed block and the corrective block. In some cases, inclusion of the corrected accumulated value in the corrected block may allow determination of the state of the accumulated value without necessarily traversing other blocks of the blockchain 199. Adding the corrective block may not necessarily alter other previously formed blocks. Accordingly, the previous (uncorrected) record entry may be maintained in the previously formed block after addition of the corrective block to the blockchain.

In an example, the correction may include a correction to a date or time for the record entry. In some cases, the consensus logic 170 may determine the need for correction be determining whether particular block reflect record entries during an affected date or time range determined based on the date of the correction. In some cases, the correction may be implemented by cancelling the effect of a previous record entry on the corrected record entry within the date range. In some cases, when a correction to the date shifts the date, the affected date range may be determined based on the period between the data before correction and the date after correction.

In another example, discussed below with regard to FIG. 12, a threshold boundary (such as a minimum or maximum) may be changed with the applicable consensus operating procedure. In some cases, this may cause a transaction initially on one side of the boundary to be moved in whole or in part to the other side. For example, a claim above a deductible maximum may be shifted below the maximum if the maximum is increased through correction. Accordingly, the effect of the claim on a deductible accum may later be accounted for by correction if the claim is later found to occur before the deductible maximum was reached. Alternatively, a claim below the maximum may be shifted above if the maximum is decreased. Accordingly, the effect of the claim on a deductible accum may later be cancelled by correction if the claim is later found to occur after the deductible maximum was reached.

When blocks may be affected by a correction (e.g., the corresponding record entries are: associated with accumulated values within an affected range, associated with dates within an affected range, or both), the consensus logic 170 may mark affected blocks or data within blocks for review (230). For example, the consensus logic 170 mark blocks by adding a review indicator referencing an affected block to the corrective block. Additionally or alternatively, consensus logic 170 may add the review indicator to metadata for affected block, which may be stored outside of the blockchain 199.

In some implementations, the blockchain may support rewrite operations on previously formed blocks. For example, trusted entities may have authority to perform rewrites to the blockchain using a secret code, key secret, cryptographic cipher, or other secret. Accordingly, corrections to record entries reflected in blocks of the blockchain may be performed by rewriting the original blocks storing the original record entry rather than adding a new corrective block and referencing the original block. In various implementations, trusted entities may include node operators, a collection of node operators that may cooperate to together serve as a trusted entity, a secure terminal under the control of a trusted operator, or other entities.

In some implementations, to preserve a clear record of corrections, trusted entities may add data to previous blocks via blockchain rewrites without necessarily removing previous data. Further, in some cases, the original data may be stored in a core portion of the blocks of the blockchain that does not support rewrite (e.g., even by trusted parties), but corrections may be added to a tertiary portion of the blocks of the blockchain that does support rewrites.

In an example health claim processing context, the consensus logic 170 may specify a set of processor-level operations including manipulation to an accum value stored within a block of the blockchain 199. The accum value may correspond to a monitored healthcare accum value, such as a deductible or out-of-pocket maximum or other healthcare-related accumulated value. For example, a claim value in the record entry may be added to the accum, subtracted from the accum, or otherwise used to update the accum value. The consensus logic 170 may then reconcile the updated accum value to other previously made entries.

For example, if a medical node corrects a past claim amount, the deductible amount available for a future claim by the medical node or other node (e.g., a pharmaceutical node) may be changed. In this context, an overage may occur when the accum value exceeds a defined threshold, such as a set out-of-pocket maximum value. In some cases, changing a past claim may lead to an overage for a claim already entered into the blockchain 199. Additionally or alternatively, changing a past claim may clear an overage that had previously been logged for another entry. Further, in some cases changes may occur as a result the system 100 entering claims out of sequence. For example, a claim related to a later occurring transaction may be entered by the system 100 before an earlier occurring transaction. This may occur as a result of out of sequence client requests or latency in updating the blockchain following a claim request.

Figure 3:
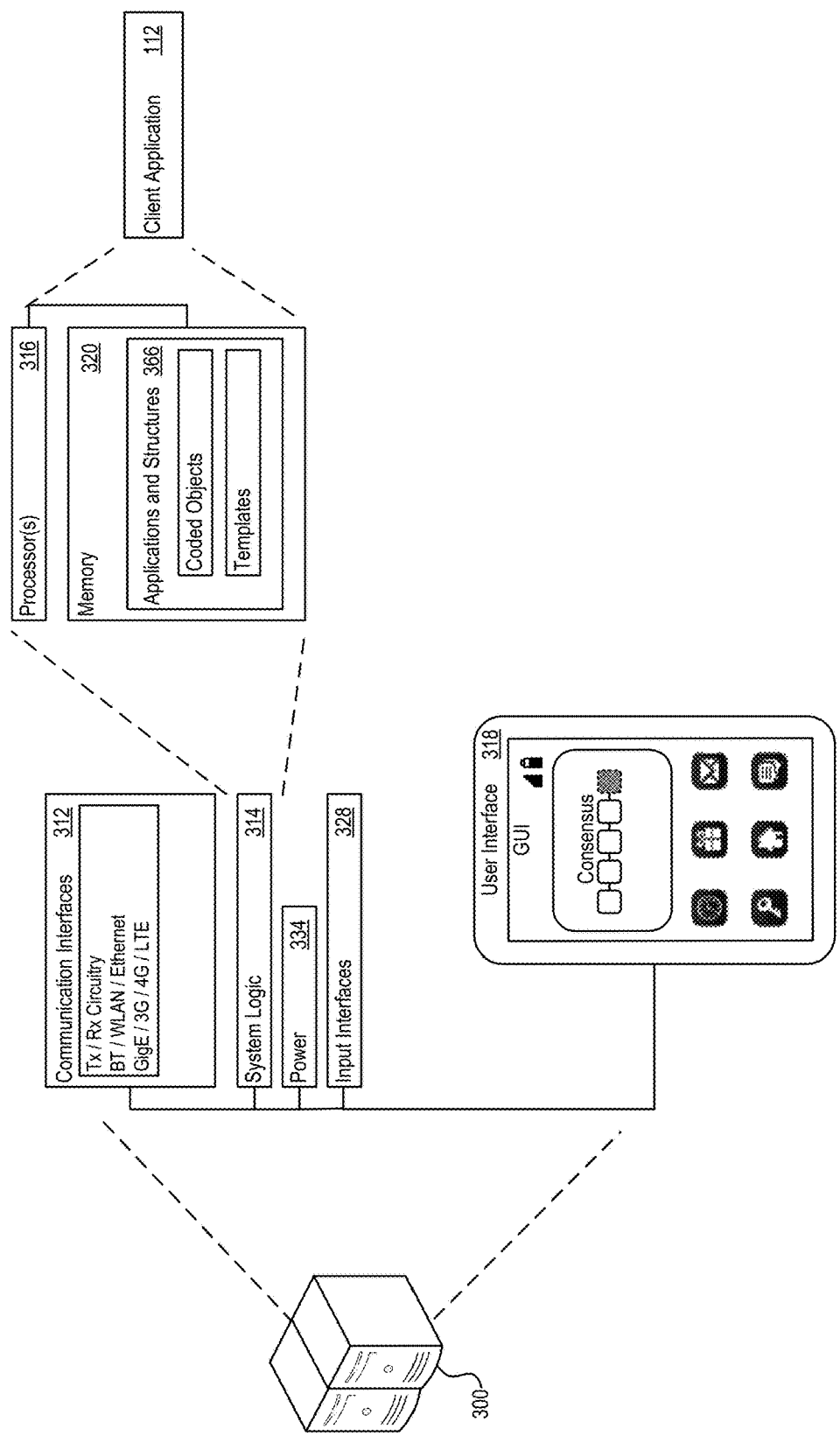
FIG. 3 shows an example client execution environment.

FIG. 3 shows an example client execution environment (CEE) 300. The example CEE 300 may serve as a hardware platform for the client circuitry 110. The CEE 300 may include system logic 314. The system logic may include processors 316, memory 320, and/or other circuitry.

The memory 320 along with the processors 316 may support execution of the client application 112. The memory 320 may further include applications and structures 366, for example, coded objects, templates, or other structures to support record information collection and submission.

The CEE 300 may also include communication interfaces 312, which may support wireless, e.g., Bluetooth, Wi-Fi, WLAN, cellular (4G, LTE/A), and/or wired, Ethernet, Gigabit Ethernet, optical networking protocols. The communication interfaces 312 may also include serial interfaces, such as universal serial bus (USB), serial ATA, IEEE 1394, lighting port, $I^2C$, slimBus, or other serial interfaces. The CEE 300 may include power functions 334 and various input interfaces 328. The CEE may also include a user interface 318 that may include human-to-machine interface devices and/or graphical user interfaces (GUI). In various implementations, the system logic 314 may be distributed over multiple physical servers and/or be implemented as a virtual machine.

In some cases the CEE 300 may be a specifically-defined computational system deployed in a cloud platform. In some cases, the parameters defining the CEE 300 may be specified in a manifest for cloud deployment. The manifest may be used by an operator to requisition cloud based hardware resources, and then deploy the logical components, for example, client application 112, of the CEE 300 onto the hardware resources. In some cases, a manifest may be stored as a preference file such as a YAML (yet another mark-up language), JavaScript object notation (JSON), or other preference file type.

Figure 4:
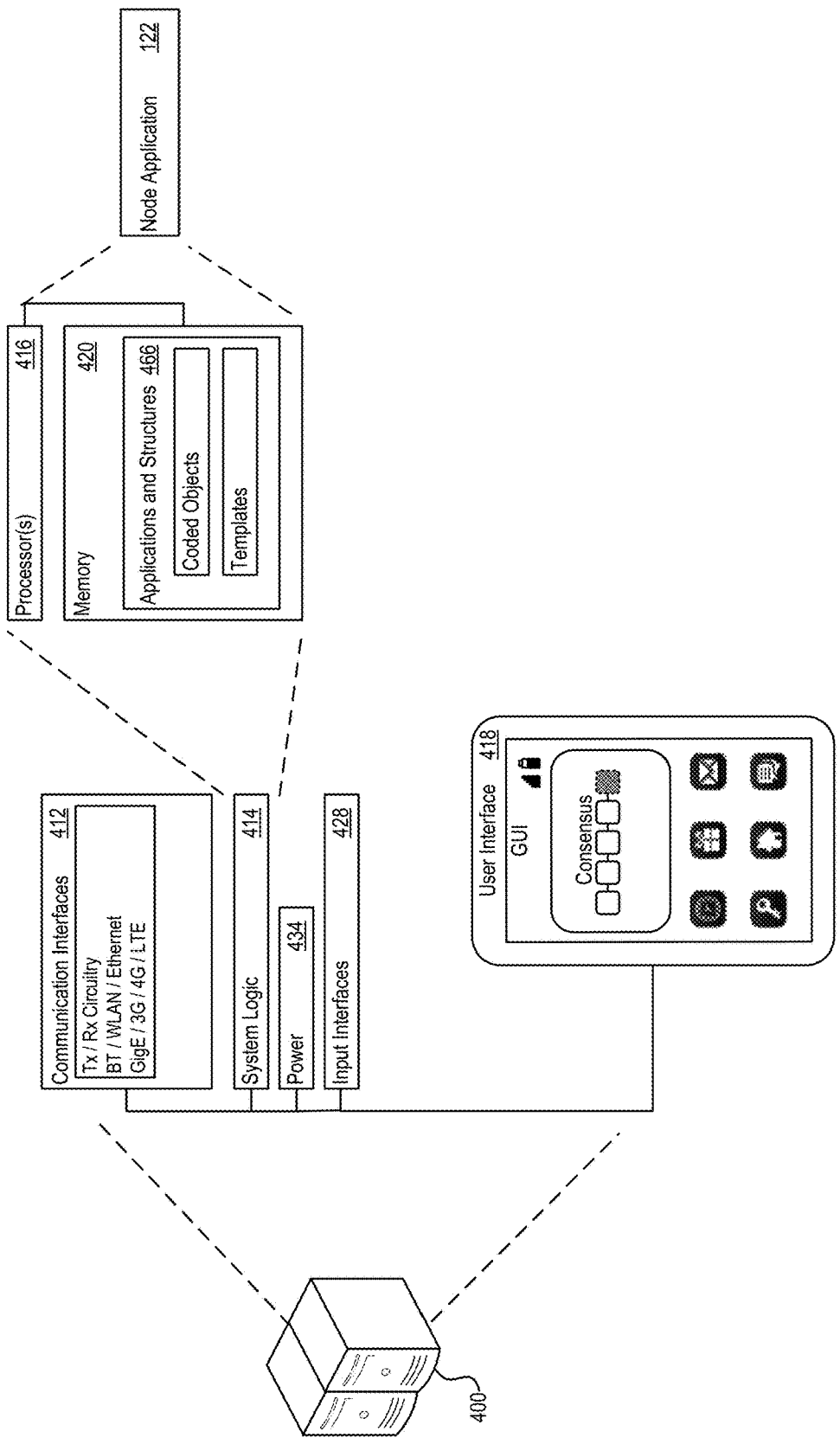
FIG. 4 shows an example node execution environment.

FIG. 4 shows an example node execution environment (NEE) 400. The example NEE 400 may serve as a hardware platform for the node circuitry 110. The NEE 400 may include system logic 414. The system logic 414 may include processors 416, memory 420, and/or other circuitry.

The memory 420 along with the processors 416 may support execution of the node application 122. The memory 420 may further include applications and structures 466, for example, coded objects, templates, or other structures to support reception of record entry information, compilation of record entries, generation of electronic forms, and interaction with the blockchain API 162.

The NEE 400 may also include communication interfaces 412, which may support wireless, e.g., Bluetooth, Wi-Fi, WLAN, cellular (4G, LTE/A), and/or wired, Ethernet, Gigabit Ethernet, optical networking protocols. The communication interfaces 412 may also include serial interfaces, such as universal serial bus (USB), serial ATA, IEEE 1394, lighting port, $I^2C$, slimBus, or other serial interfaces. The NEE 400 may include power functions 434 and various input interfaces 428. The NEE 400 may also include a user interface 418 that may include human-to-machine interface devices and/or graphical user interfaces (GUI). In various implementations, the system logic 414 may be distributed over multiple physical servers and/or be implemented as a virtual machine.

In some cases the NEE 400 may be a specifically-defined computational system deployed in a cloud platform. In some cases, the parameters defining the NEE may be specified in a manifest for cloud deployment. The manifest may be used by an operator to requisition cloud based hardware resources, and then deploy the logical components, for example, the node application 122, of the NEE 400 onto the hardware resources. In some cases, a manifest may be stored as a preference file such as a YAML (yet another mark-up language), JSON, or other preference file type.

Figure 5:
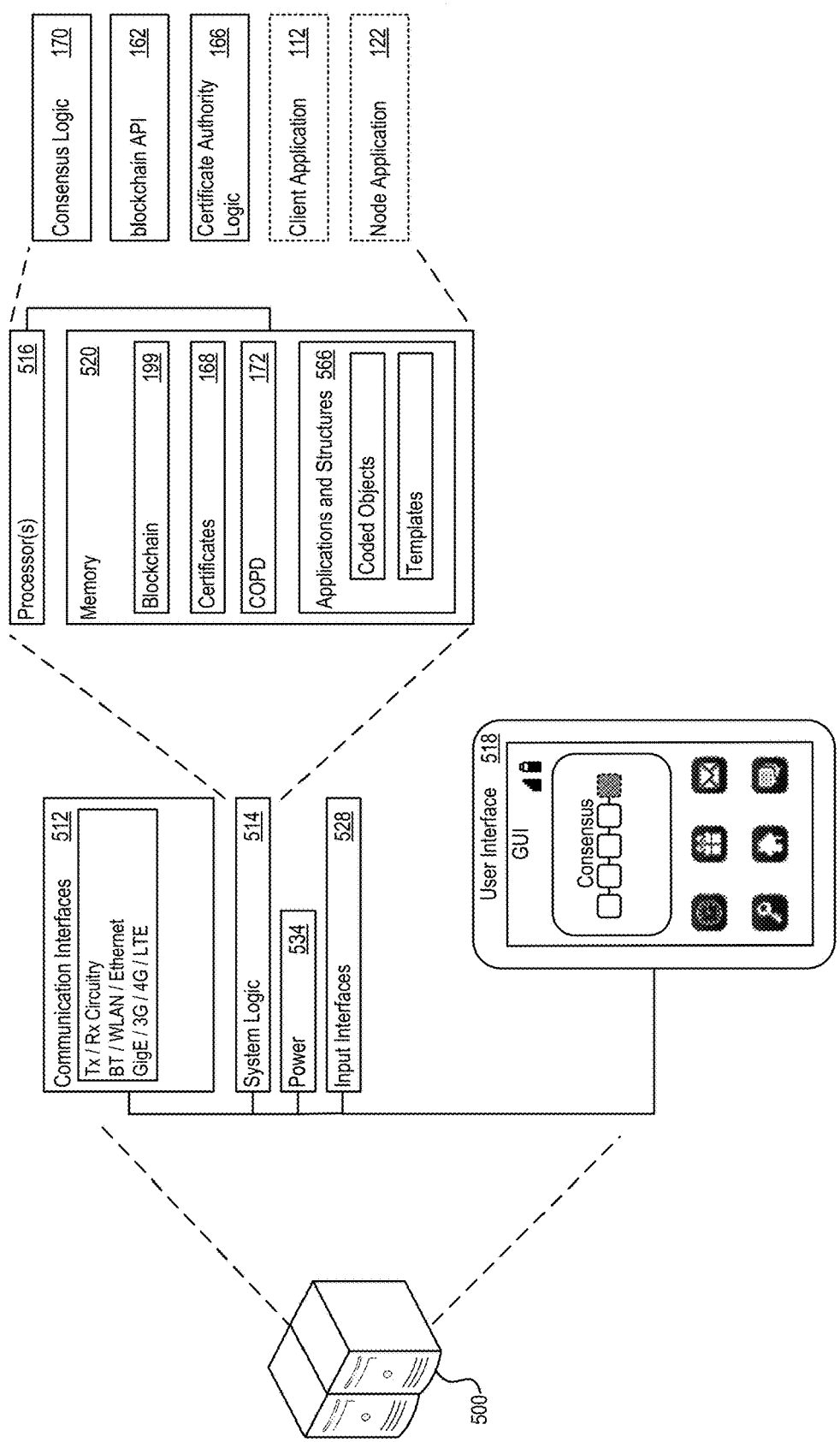
FIG. 5 shows an example accelerated blockchain execution environment.

FIG. 5 shows an example accelerated blockchain execution environment (ACEE) 500. The example ACEE 500 may serve as a hardware platform for the BMC 160. However, in some implementations, the ACEE 500 may be adapted to support integration with the client circuitry 110, node circuitry 120, or both. The ACEE 500 may include system logic 514. The system logic 514 may include processors 516, memory 520, and/or other circuitry.

The memory 520 may be include the blockchain 199, certificates 168, and consensus operation procedure definitions (COPD) 172. The memory 520 may further include applications and structures 566, for example, coded objects, templates, or other structures to support blockchain transaction acceleration, operational procedure implementation, certificate authority management, or other blockchain transactions. The memory 520 and processors 516 may support execution of the blockchain API 162, consensus logic 170, and certificate authority logic 166.

The ACEE 500 may also include communication interfaces 512, which may support wireless, e.g., Bluetooth, Wi-Fi, WLAN, cellular (4G, LTE/A), and/or wired, Ethernet, Gigabit Ethernet, optical networking protocols. The communication interfaces 512 may also include serial interfaces, such as universal serial bus (USB), serial ATA, IEEE 1394, lighting port, $I^2C$, slimBus, or other serial interfaces. The ACEE 500 may include power functions 534 and various input interfaces 528. The ACEE may also include a user interface 518 that may include human-to-machine interface devices and/or graphical user interfaces (GUI). In various implementations, the system logic 514 may be distributed over multiple physical servers and/or be implemented as a virtual machine.

In some cases the ACEE 500 may be a specifically-defined computational system deployed in a cloud platform. In some cases, the parameters defining the ACEE may be specified in a manifest for cloud deployment. The manifest may be used by an operator to requisition cloud based hardware resources, and then deploy the logical components, for example, consensus logic 170, of the ACEE onto the hardware resources. In some cases, a manifest may be stored as a preference file such as a YAML (yet another mark-up language), .JSON, or other preference file type.

In some implementations, the accelerated record entry hardware 100 may manage claims in a healthcare context. The record entry 124 and record entry information 114 may include multiple fields designating values associated with particular claims. Table 1 below shows an example record entry fields that may be included in an example record entry 124 and/or conveyed by the record entry information 112.

TABLE 1

Example Record Entry Fields

| Field | Definition | Data Type | Number |
| --- | --- | --- | --- |
| Timestamp | Date/Time of transaction posted to ledger | Timestamp | 1 |
| Transaction ID | Unique identifier for ledger transaction | Numeric | 2 |

TABLE 1-continued

Example Record Entry Fields

| Field | Definition | Data Type | Number |
| --- | --- | --- | --- |
| Claim ID | Unique identifier allowing tie-back to claims system that processed this transaction prior to posting to ledger | Numeric | 3 |
| Subscriber ID | Identifies subscriber to Health Policy | Numeric | 4 |
| Member ID (Foreign Key to Member Demographics) | Identifies individual who received care | Numeric | 5 |
| Policy ID | Identifies the Benefit Plan Policy associated for this transaction | Numeric | 6 |
| Accumulator Type | Accumulators are allocated to Members of Health Policy to track liability. One member may have multiple Accumulator types. | String | 7 |
| Accumulation Start Date | Date that Accumulator begins tracking transactions | Timestamp | 8 |
| Accumulation End Date | Date that Accumulator ends tracking transactions | Timestamp | 9 |
| Participant | Source organization/party that posted transaction | String | 10 |
| Unit of Measure | Metric for Accumulator transactions and balances | String | 11 |
| Transaction Amount | Amount recorded for a transaction | Numeric | 12 |
| Sex | Identifies male or female | String | 13 |
| Date of Birth | Identifies birthdate of member | Date | 14 |
| Last Name | Identifies last name of member | String | 15 |
| First Name | Identifies first name of member | String | 16 |
| Relationship | Identifies whether subscriber or dependent (e.g. child or spouse) | String | 17 |
| Date of Service | Identifies date of when member received care | Date | 18 |
| Provider/ Facility | Name of service provider (e.g. Hospital/Physician/Pharmacy) where member received care | String | 19 |
| Claim Amount | $ amount submitted on claim for service | Numeric | 20 |

The record entries 124 may include any or all of the above fields. For example, a record entry for an accum transaction may include fields 1-12, a member demographic record entry may include fields 4, 5 and 13-17, a record entry for a claim may include fields 5, 16, and 18-20. However, other combination of fields are possible.

In addition to defining fields for entries, a healthcare implementation may define accums for various values tracked by the system 100. These values may be monetary, but also may include other defined values, such as service visit tracking, dosage tracking, or other values. The system 100 may define a time window for tracking including, hourly, daily, weekly, monthly, yearly, multiple-year periods, or other defined time frames. The accum may reset at the end of the timeframe, roll-over, or remain unchanged. The behavior of the accum may be defined using the consensus operating procedure.

Table 2 shows example accums for the healthcare transaction context.

TABLE 2

Example Accum Types

| Accumulator Types | Used for | Definition |
|---|---|---|
| IIDED | In-Network Individual Deductible | Amount paid by patient/member until insurance coverage initiates. E.g. $500 Deductible means the patient must pay $500 before their insurance covers certain services |
| IFDED | In-Network Family Deductible | Amount paid by full family until insurance coverage initiates. E.g. $500 Deductible means the patient must pay $500 before their insurance covers certain services |
| OIDED | Out-of-Network Individual Deductible | Amount paid by patient/member until insurance coverage initiates. E.g. $500 Deductible means the patient must pay $500 before their insurance covers certain services |
| OFDED | Out-of-Network Family Deductible | Amount paid by full family until insurance coverage initiates. E.g. $500 Deductible means the patient must pay $500 before their insurance covers certain services |
| IIOOP | In-Network Individual Out-of-Pocket | Amount member/patient has paid towards services to date. E.g. If member paid $500 towards their deductible + were covered at 80% for a $100 service (i.e. insurance covered $80) then the total Out of Pocket balance would be $520 |
| IFOOP | In-Network Family Out-Of-Pocket | Amount member/patient has paid towards services to date. E.g. If member paid $500 towards their deductible + were covered at 80% for a $100 service (i.e. insurance covered $80) then the total Out of Pocket balance would be $520 |
| OIOOP | Out-of-Network Individual Out-of-Pocket | Amount member/patient has paid towards services to date. E.g. If member paid $500 towards their deductible + were covered at 80% for a $100 service (i.e. insurance covered $80) then the total Out of Pocket balance would be $520 |
| OFOOP | Out-of-Network Family Out-of-Pocket | Amount member/patient has paid towards services to date. E.g. If member paid $500 towards their deductible + were covered at 80% for a $100 service (i.e. insurance covered $80) then the total Out of Pocket balance would be $520 |
| COPAY | Copayment | Fixed amount a patient/member has agreed to pay for specific services. E.g. a general doctor Office Visit may have a $20 Copay. That means Member always pays that $20, rather than a % coverage |

For the defined accums types, the system 100 may have defined operational procedures. The consensus operating procedures may be defined using computer code or scripting languages to reduce operational ambiguity.

Table 3 shows example pseudocode specifying a consensus operating procedure for updating an IIDED accum in response to a claim filing.

TABLE 3

Example IIDED Consensus operating procedure Pseudocode

| Action | Pseudocode |
|---|---|
| Update Accums—DED | If <balance> < <Ded Limit> then: If <accum type> = IIDED and if <Transaction Amount> + <balance> <= <Ded Limit> then <balance> = (<balance> + <Transaction Amount>) |
| Calculate Overage Amount | If< accum type> = IIDED and if <Transaction Amount> + <balance> > <Ded Limit> Then <Overage Amount> = ( <Transaction Amount> + <balance> − <Ded Limit>) and <balance> = <Ded Limit> |
| Accums have been met | Else, Limit has been reached no new accum updates |

Table 4 shows example pseudocode specifying a consensus operating procedure for updating an IIOOP accum in response to a claim filing.

TABLE 4

Example IIOOP Consensus operating procedure Pseudocode

| Action | Pseudocode |
|---|---|
| Update Accums—OOP | If <balance> < <OOP Limit> then: If <accum type> = IIOOP and if <Transaction Amount> + <balance> <= <OOP Limit> then <balance> = (<balance> + <Transaction Amount>) |
| Calculate Overage Amount | If<accum type> = IIOOP and if <Transaction Amount> + <balance> > <OOP Limit> Then <Overage Amount> = ( <Transaction Amount> + <balance> − <OOP Limit>) and <balance> = <OOP Limit> |
| Accums have been met | Else, Limit has been reached no new accum updates |

Table 5 shows example pseudocode specifying a consensus operating procedure for updating an IFDED accum in response to a claim filing.

TABLE 5

Example IFDED Consensus operating procedure Pseudocode

| Action | Pseudocode |
|---|---|
| Update Accums—DED | If <Subscriber balance> < <Fam Ded Limit> then:<br>If <accum type> = IFDED<br>and if <Transaction Amount> + <subscriber balance> <= <Fam Ded Limit> then <subscriber balance> = (<subscriber balance> + <Transaction Amount>) |
| Calculate Overage Amount | If< accum type> = IFDED<br>and if <Transaction Amount> + <subscriber balance> > <Fam Ded Limit><br>Then <Overage Amount> = ( <Transaction Amount> + <Subscriber balance> – <Fam Ded Limit>)<br>and <<subscriber balance> = <Fam Ded Limit> |
| Accums have been met | Else, Limit has been reached no new accum updates |

Table 6 shows example pseudocode specifying a consensus operating procedure for updating an IFOOP accum in response to a claim filing.

TABLE 5

Example IFOOP Consensus operating procedure Pseudocode

| Action | Pseudocode |
|---|---|
| Update Accums—OOP | If <Subscriber balance> < <Fam DOOP Limit> then:<br>If <accum type> = IFOOP<br>and if <Transaction Amount> + <subscriber balance> <= <Fam OOP Limit> then <subscriber balance> = (<subscriber balance> + <Transaction Amount>) |
| Calculate Overage Amount | If< accum type> = IFOOP<br>and if <Transaction Amount> + <subscriber balance> > <Fam OOP Limit><br>Then <Overage Amount> = ( <Transaction Amount> + <Subscriber balance> – <Fam OOP Limit>)<br>and <<subscriber balance> = <Fam Ded Limit> |
| Accums have been met | Else, Limit has been reached no new accum updates |

The above example consensus operational process definitions (Tables 3-6) show specific procedures that may be agreed upon by multiple parties using a blockchain. The precise definition of rules may facilitate the verifiability of compliance to the consensus operating procedures by parties reviewing the contents of blocks in the blockchain. When rules a specified such that outputs are deterministic once the inputs are set, the system 100 may verify that the posting of a block to the blockchain is compliant by applying the consensus operating procedure to the input and confirming that the output stored in the block matches the obtained value. Additionally or alternatively, validity indicators may be verified for authenticity.

In the example health claims context, the accums may be used to track and classify claims activity among multiple providers. In some cases, the claims may be processed and applied the accum in real-time or near real-time once the provider submits record entry information with the claims details. In some cases, access to real-time tracking for accums may increase the value of a health services to subscribers and members because they may use the continually updated information to better guide real-time health services decisions.

Figure 6:
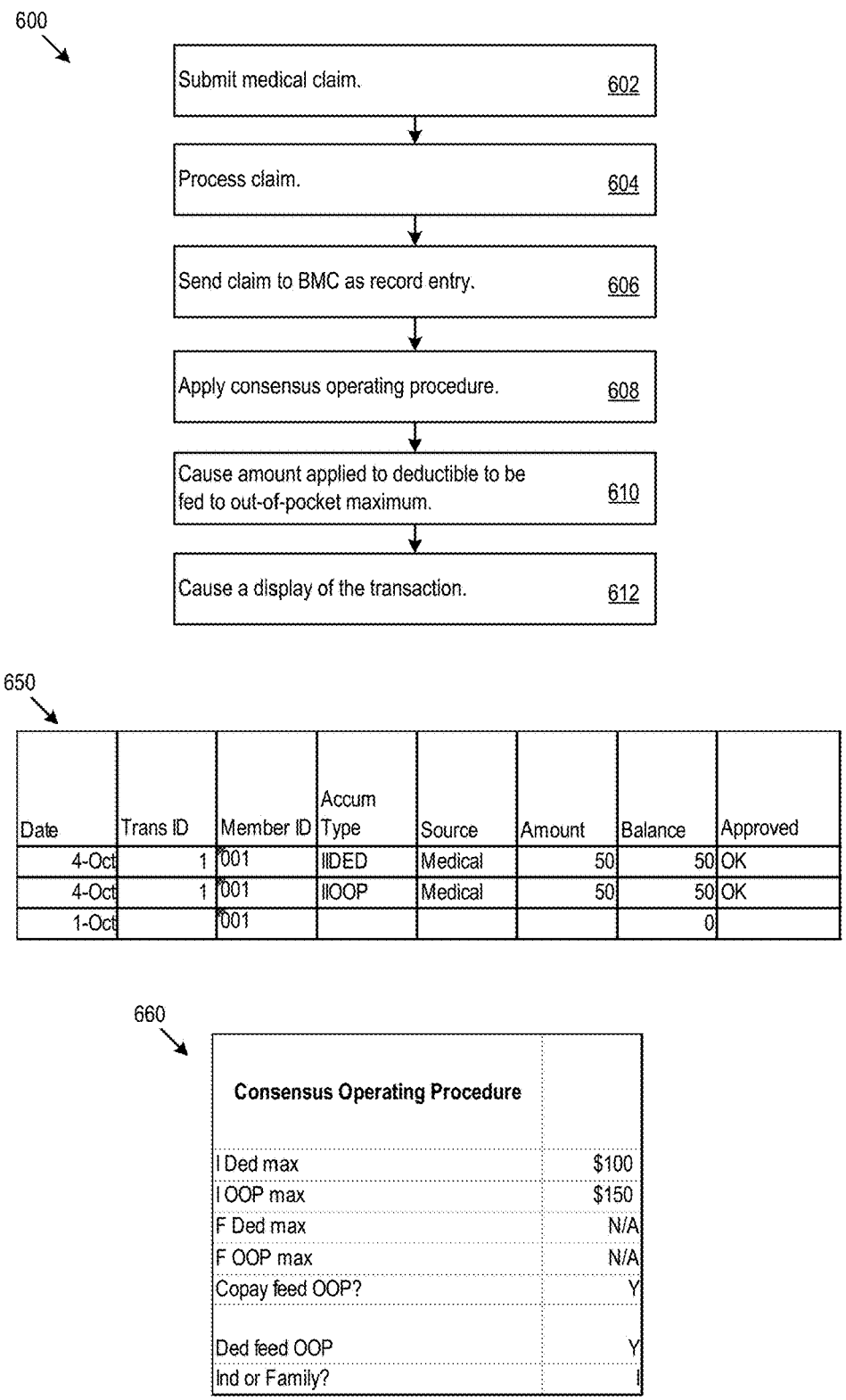
FIG. 6 shows an example usage scenario for the example accelerated record entry hardware system of FIG. 1.

FIG. 6 shows an example of an execution-environment-implemented usage scenario 600 for the example accelerated record entry hardware system 100. For example, the usage scenario 600 and those below (700-1200) may be implemented on any or all of the CEE 300, NEE 400, or ACEE 500. In the usage scenario 600, a provider submits a medical claim 602). A medical node processes the claim 604). The medical node sends the claim to the BMC as a record entry (606). The BMC applies the consensus operating procedure 660 (608). In accord with the procedure, the Ded feed OOP rule causes the amount applied to the deductible to be fed to the out-of-pocket maximum (610). The BMC causes a display of the transaction on a user interface (612). The processor-level operations on the values are shown in the output sequence 650.

Figure 7:
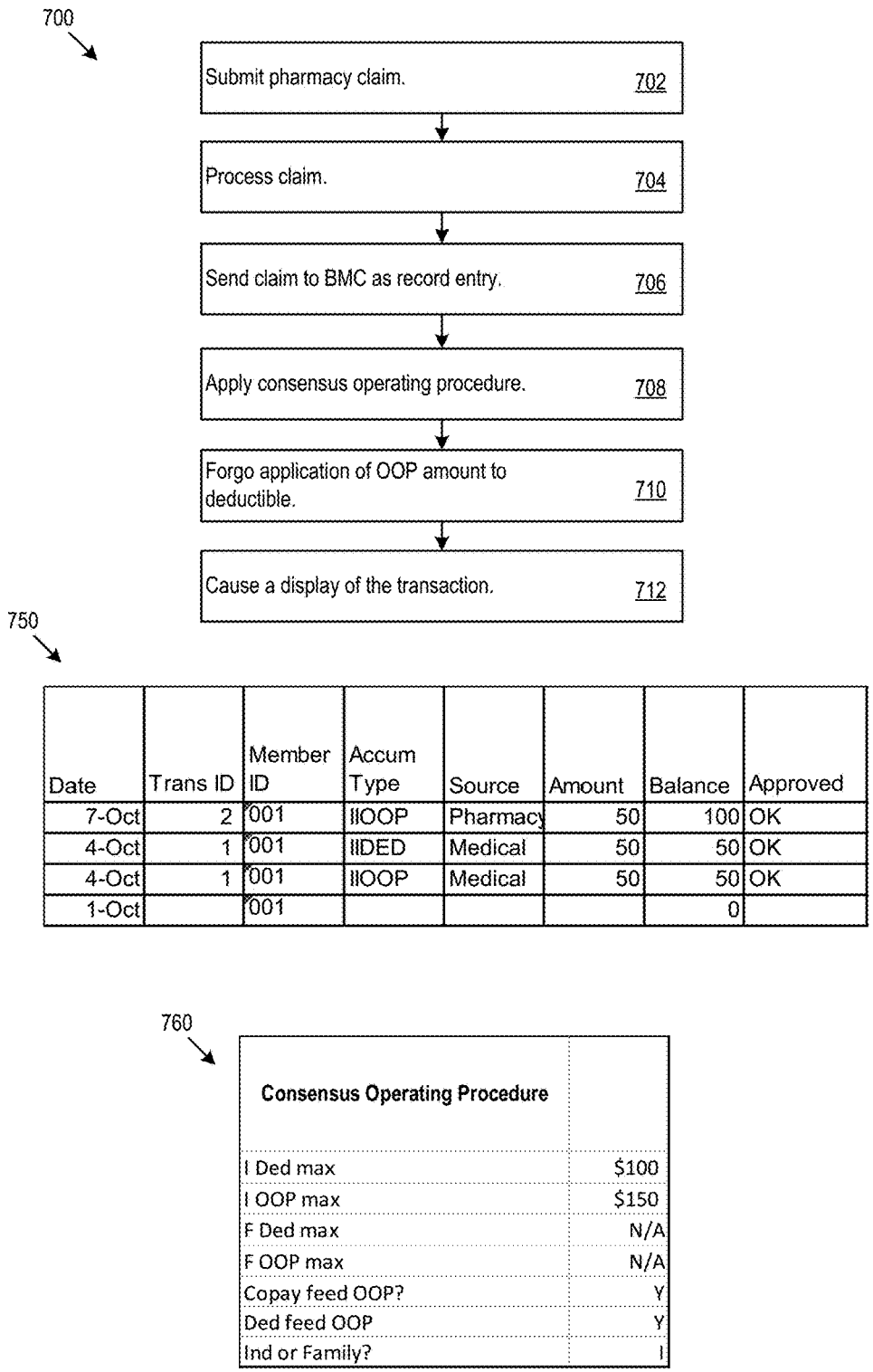
FIG. 7 shows an example usage scenario for the example accelerated record entry hardware system of FIG. 1.

FIG. 7 shows an example execution-environment-implemented usage scenario 700 for the example accelerated record entry hardware system 100. In the usage scenario 700, a provider submits a pharmacy claim 702). A pharmacy node processes the claim 704). The pharmacy node sends the claim to the BMC as a record entry (706). The BMC applies the consensus operating procedure 760 (708). In accord with the procedure, the OOP is not applied to the deductible (710). The BMC causes a display of the transaction on a user interface (712). The processor-level operations on the values are shown in the output sequence 750.

Figure 8:
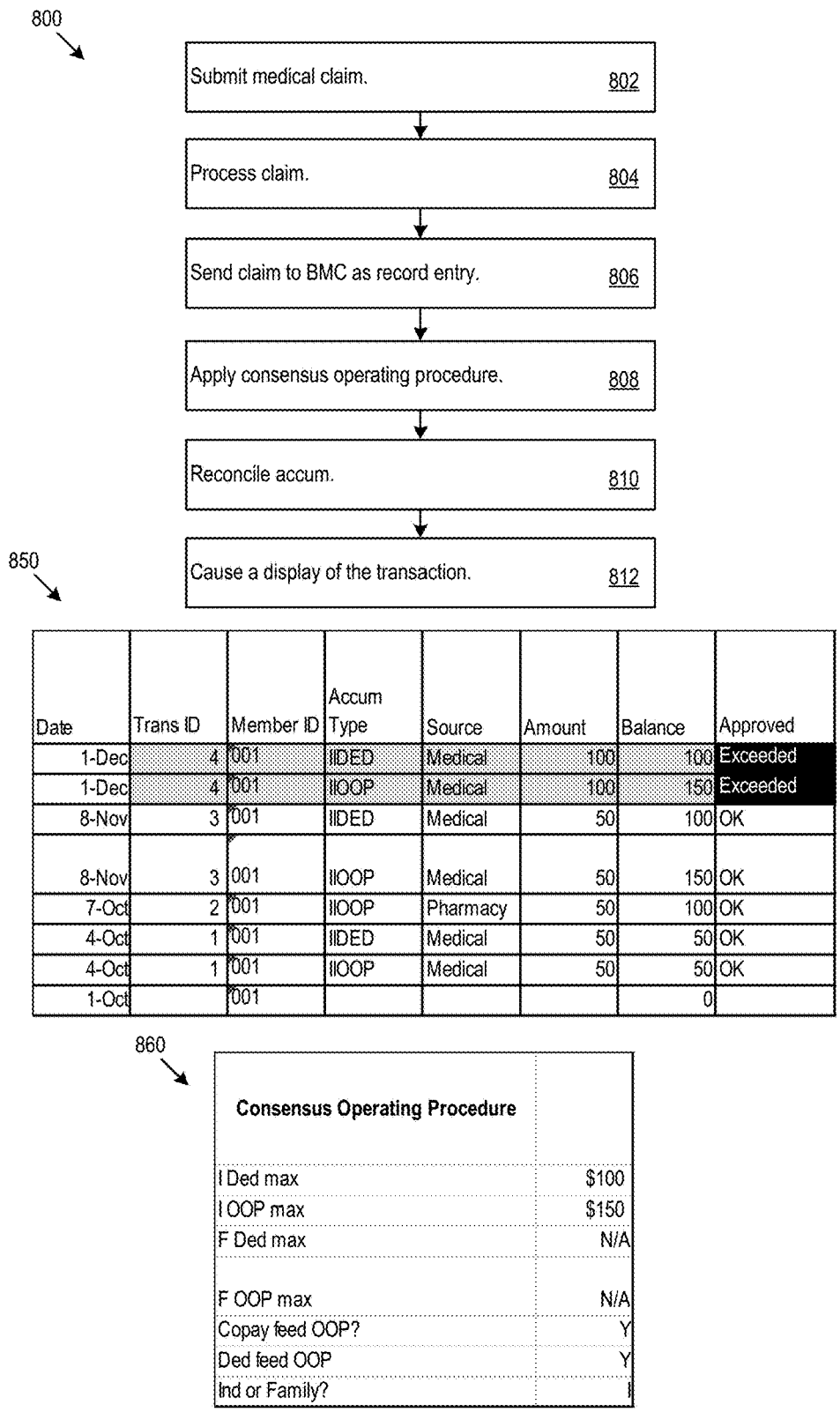
FIG. 8 shows an example usage scenario for the example accelerated record entry hardware system of FIG. 1.

FIG. 8 shows an example execution-environment-implemented usage scenario 800 for the example accelerated record entry hardware system 100. In the usage scenario 800, a provider submits a medical claim 802). A medical node processes the claim 804). The medical node sends the claim to the BMC as a record entry (806). The BMC applies the consensus operating procedure 860 (808). In accord with the procedure, the BMC reconciles the accum across the multiple nodes and identifies overages (810). The BMC causes a display of the transaction on a user interface (812). The processor-level operations on the values are shown in the output sequence 850.

Figure 9:
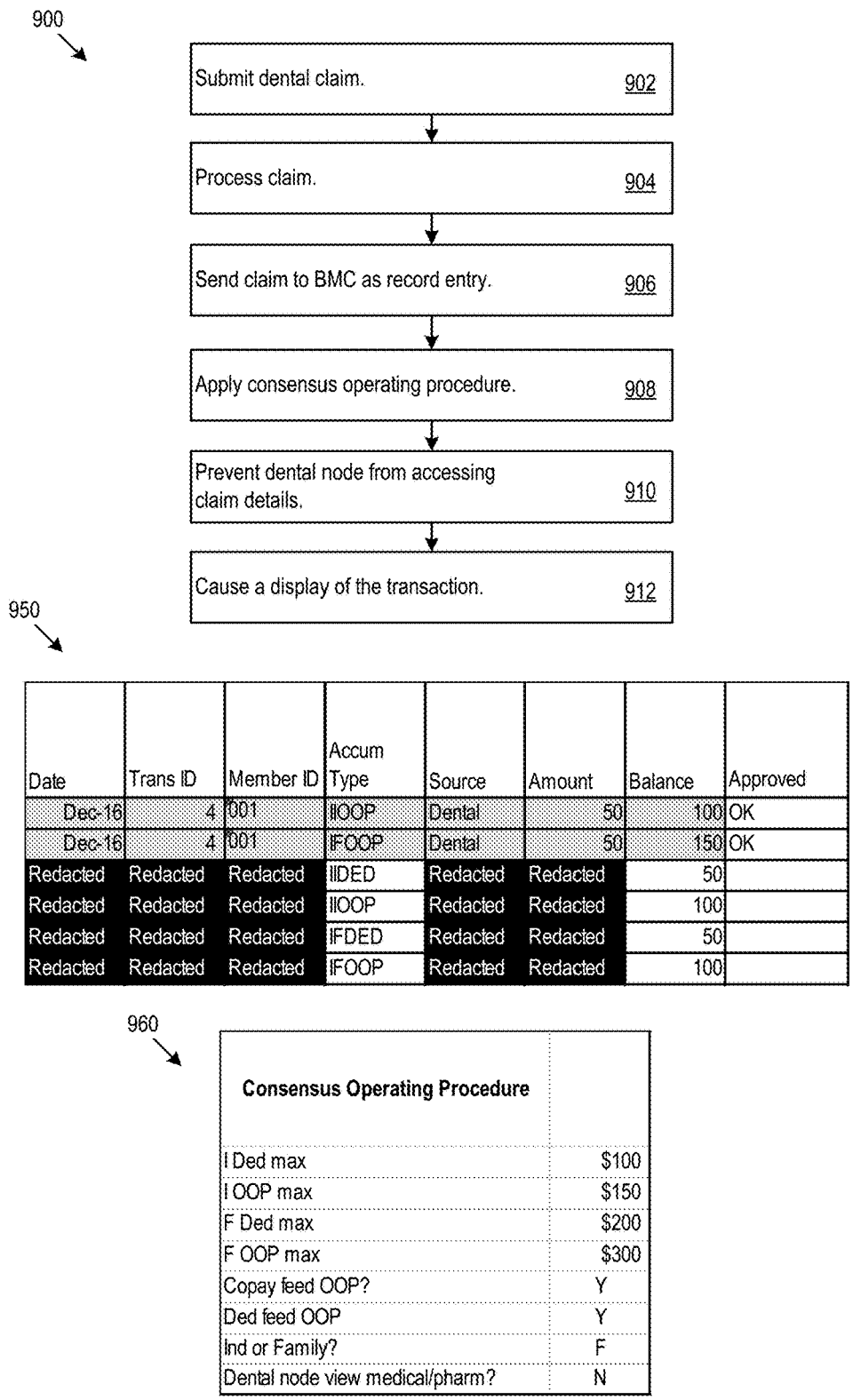
FIG. 9 shows an example usage scenario for the example accelerated record entry hardware system of FIG. 1.

FIG. 9 shows an example execution-environment-implemented usage scenario 900 for the example accelerated record entry hardware system 100. In the usage scenario 900, a provider submits a dental claim 902). A dental node processes the claim 904). The dental node sends the claim to the BMC as a record entry (906). The BMC applies the consensus operating procedure 960 (908). In accord with the procedure, the BMC prevents the dental node from accessing details regarding medical and pharmacy claims 910). The BMC causes a display of the transaction on a user interface (912). The processor-level operations on the values are shown in the output sequence 950. In accord with the access restrictions for the detail node, details from some claims are redacted from the output sequence.

Figure 10:
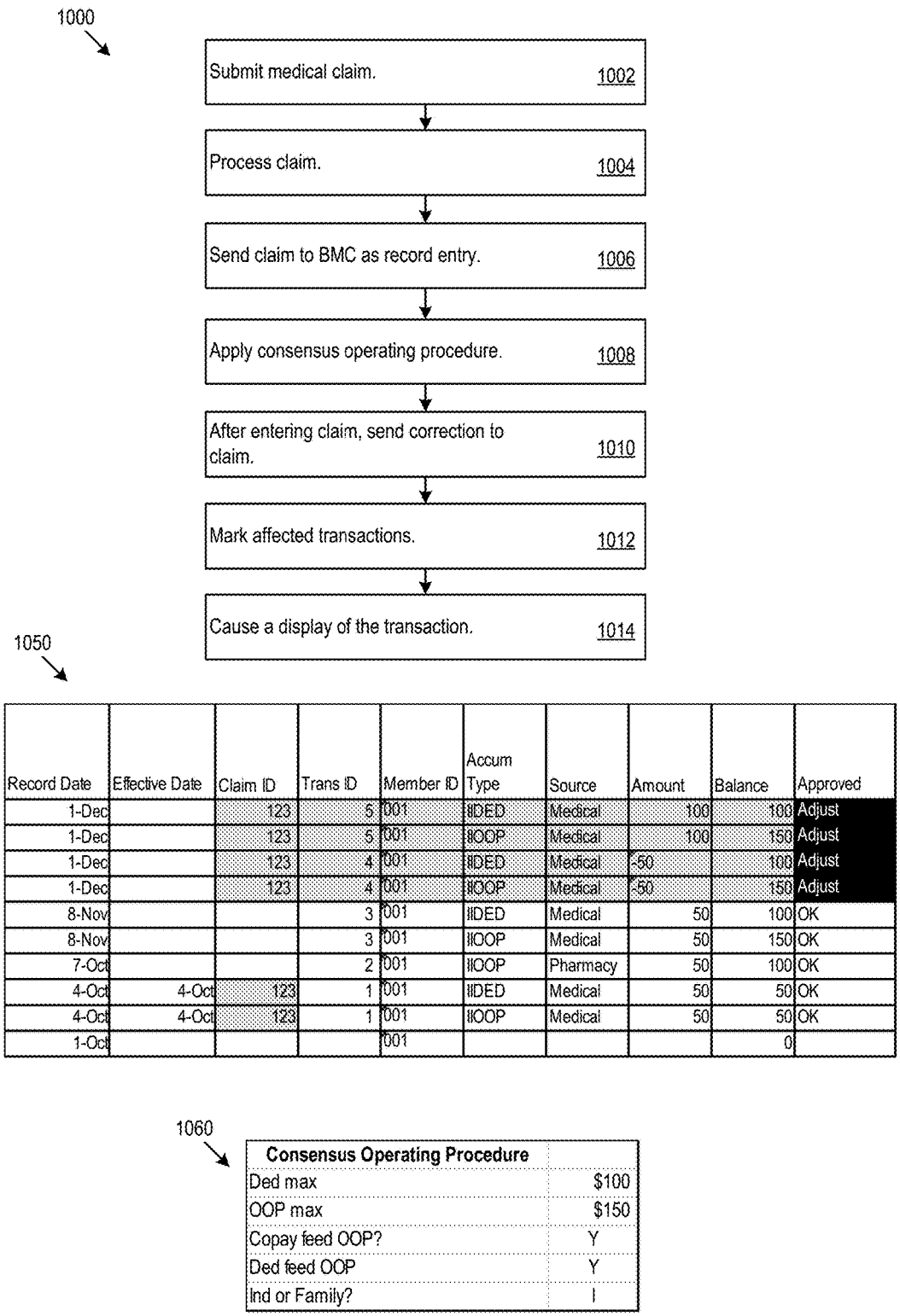
FIG. 10 shows an example usage scenario for the example accelerated record entry hardware system of FIG. 1.

FIG. 10 shows an example execution-environment-implemented usage scenario 1000 for the example accelerated record entry hardware system 100. In the usage scenario 1000, a provider submits a medical claim 1002). A medical node processes the claim 1004). The medical node sends the claim to the BMC as a record entry (1006). The BMC applies the consensus operating procedure 1060 (1008). The medical node later sends a correction to the claim by reference the claim ID (1010). The BMC marks affected transactions for adjustment (1012). The BMC causes a display of the transaction on a user interface (1014). The processor-level operations on the values are shown in the output sequence 1050.

Figure 11:
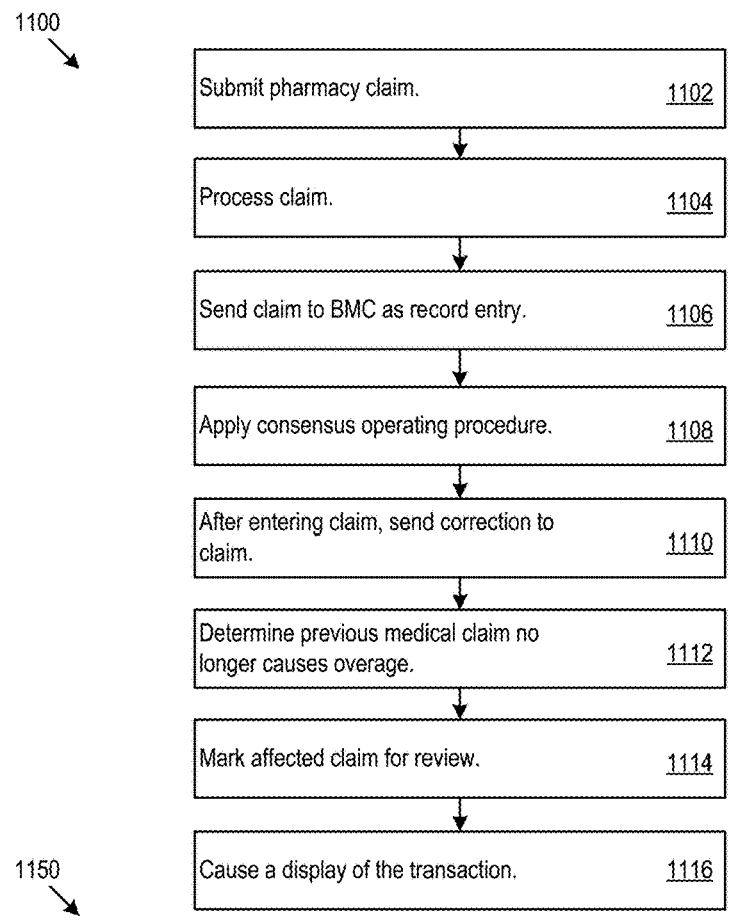
FIG. 11 shows an example usage scenario for the example accelerated record entry hardware system of FIG. 1.

FIG. 11 shows an example execution-environment-implemented usage scenario 1100 for the example accelerated record entry hardware system 100. In the usage scenario 1100, a provider submits a pharmacy claim 1102). A pharmacy node processes the claim 1104). The pharmacy node sends the claim to the BMC as a record entry (1106). The BMC applies the consensus operating procedure 1160 (1108). The pharmacy node later sends a correction to the pharmacy claim by reference the claim ID, "CL57" (1110). The reduction in response to the corrected claim, causes a previous medical claim to no longer cause an overage (1112). The BMC marks the affected claim for review (1114). The BMC causes a display of the transaction on a user interface (1116). The processor-level operations on the values are shown in the output sequence 1150.

Figure 12:
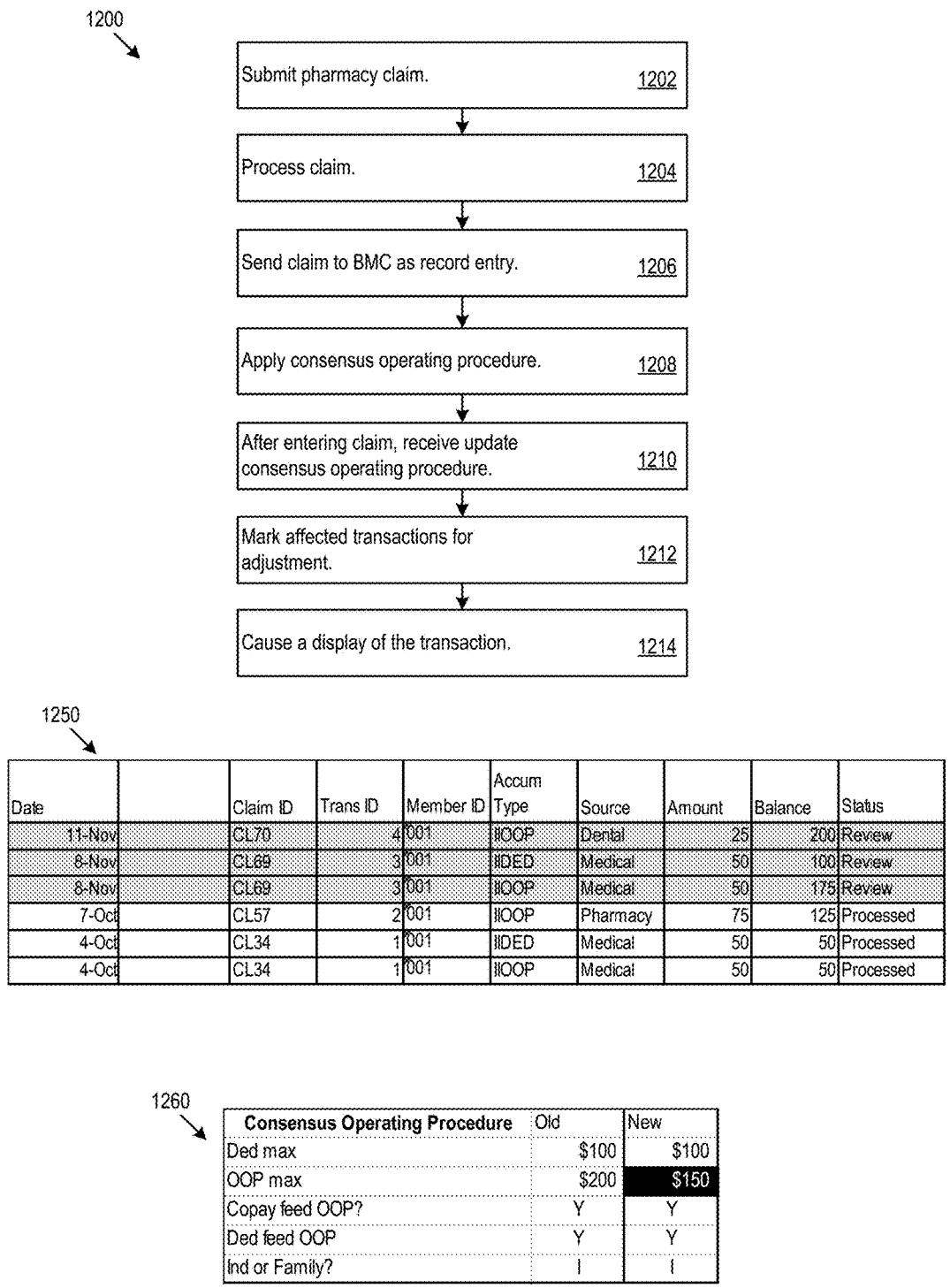
FIG. 12 shows an example usage scenario for the example accelerated record entry hardware system of FIG. 1.

FIG. 12 shows an example execution-environment-implemented usage scenario 1200 for the example accelerated record entry hardware system 100. In the usage scenario 1200, a provider submits a pharmacy claim 1202). A pharmacy node processes the claim 1204). The pharmacy node sends the claim to the BMC as a record entry (1206). The BMC applies the consensus operating procedure 1260 (1208). The BMC later receives an updated to the consensus operating procedure that adjusts a maximum amount for an out-of-pocket accum (1210). In this example case, the OOP maximum is changed from $200 to $150. The BMC marks affected transactions for adjustment (1212). The BMC causes a display of the transaction on a user interface (1214). The processor-level operations on the values are shown in the output sequence 1250.

In the various usage scenarios, the BMC may mark claims for review by adding flag bits with the claim ID to the blockchain. The flag bits may cause the node circuitry to generate prompts to initiate manual review of the affected claims. Additionally or alternatively, the BMC may initiate corrective action. For example, the BMC may send a message that causes the node circuitry to issue refunds or send additional invoicing.

The usage scenarios in the health claims context were described above with regard to the accelerated record entry hardware system 100. However, the accelerated record entry hardware system 100 may be used to track other accumulated values. For example, the accelerated record entry hardware system 100 may be used in maintaining a record of network usage for telecommunication service provision. For example, user equipment may post usage to a blockchain. The blockchain may be used by the provider to track usage. The blockchain may be used to ensure that the user equipment does not alter the usage record if compromised. Additionally or alternatively, the blockchain may be applied in multiple telecommunication provider contexts. For example, multiple providers may wish to coordinate complementary services, such as regional wireless coverage, television and cellular service, or other combinations of service. The blockchain of the accelerated record entry hardware system 100 may be used as a multiple-provider record for tracking usage of the difference services. The consensus operating procedure may be used to ensure the multiple providers adhere to agreed-upon tracking standards. The accelerated record entry hardware system 100 may be used in virtually any context where multiple parties agree to a consensus operating procedure for additions to a blockchain.

In an example, a method may include, in a record entry hardware system: receiving, at a blockchain management circuitry (BMC), a record entry from node circuitry; responsive to an identity of the node circuitry, applying a consensus operating procedure to generate a new accumulated value by performing a processor-level operation using a previous accumulated value and the record entry as inputs, the previous accumulated value stored within a selected block of the blockchain; and generating a new block for the blockchain responsive to new accumulated value and a hash value generated using content of a previous block on the blockchain.

In various implementations, the method may further include: accessing, in memory on the BMC, a definition for the consensus operating procedure responsive to the blockchain and the identity of the node circuitry.

In various implementations, the method may further include: response to an identity of the node circuitry, obtaining a certificate configured to grant access to a portion of a blockchain; and determining that the record entry applies to the portion of the blockchain.

In various implementations, applying the consensus operating procedure may include updating a health accum value.

In various implementations, the consensus operating procedure may be defined using a smart contract.

In various implementations, the hash value may prevent non-tamper-evident alteration of the previous block.

In various implementations, generating the new block may further include generating the new block responsive to completion of the consensus operating procedure.

In various implementations, the selected block and the previous block may be the same block.

In various implementations, the method may further include: obtaining a validity indicator responsive to completion of the consensus operating procedure.

In various implementations, the node circuitry may be configured to generate the record entry from record entry information received from client circuitry.

In various implementations, the node circuitry may be configured to receive the record entry information from an electronic form hosted by the node circuitry.

In another example, a system may be configured to implement one or more of the methods described above.

The methods, devices, architectures, processing, circuitry, and logic described above may be implemented in many different ways and in many different combinations of hardware and software. For example, all or parts of the implementations may be circuitry that includes an instruction processor, such as a Central Processing Unit (CPU), microcontroller, or a microprocessor; or as an Application Specific Integrated Circuit (ASIC), Programmable Logic Device (PLD), or Field Programmable Gate Array (FPGA); or as circuitry that includes discrete logic or other circuit components, including analog circuit components, digital circuit components or both; or any combination thereof. The circuitry may include discrete interconnected hardware components or may be combined on a single integrated circuit die, distributed among multiple integrated circuit dies, or implemented in a Multiple Chip Module (MCM) of multiple integrated circuit dies in a common package, as examples.

Accordingly, the circuitry may store or access instructions for execution, or may implement its functionality in hardware alone. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed. For instance, the circuitry may include multiple distinct system components, such as multiple processors and memories, and may span multiple distributed processing systems. Parameters, databases, and other data structures may be separately stored and managed, may be incorporated into a single memory or database, may be logically and physically organized in many different ways, and may be implemented in many different ways. Example implementations include linked lists, program variables, hash tables, arrays, records (e.g., database records), objects, and implicit storage mechanisms. Instructions may form parts (e.g., subroutines or other code sections) of a single program, may form multiple separate programs, may be distributed across multiple memories and processors, and may be implemented in many different ways. Example implementations include stand-alone programs, and as part of a library, such as a shared library like a Dynamic Link Library (DLL). The library, for example, may contain shared data and one or more shared programs that include instructions that perform any of the processing described above or illustrated in the drawings, when executed by the circuitry.

Various implementations have been specifically described. However, many other implementations are also possible. For instance, any of the components and functionality in the architecture may be hosted in virtual machines managed by a cloud services provider. That is, while some implementations may be completely localized within a given enterprise, other implementations are completely migrated into the cloud, or are hybrid implementations with mixed local and cloud implementation. Regarding querying devices, the smartphones applications and desktop computers noted above are just particular examples, and other querying devices may be used, including hands-free systems in vehicles, digital personal assistants in smartphones or desktop PCs, hands-free control systems for the home, and many other types of devices.

What is claimed is:

1. A method including:
   in a record entry hardware system:
      determining, at blockchain management circuitry (BMC), that a previous record entry stored within a blockchain is erroneous;
      after determining that the previous record entry is erroneous, determining, at the BMC, a correction for the previous record entry;
      accessing, in memory within the BMC, an identifier of a particular consensus operating procedure;
      selecting the particular consensus operating procedure from among multiple consensus operating procedures defined within the memory,
         the particular consensus operating procedure selected responsive to the blockchain;
      obtaining a previous accumulated value stored within a previous valid block of the blockchain and generated without the correction, the previous valid block being valid based on consistence between the previous valid block and a previous hash stored within the blockchain;
      applying the particular consensus operating procedure to generate a corrected accumulated value from the previous accumulated value, where the applying includes:
         marking the previous record entry as erroneous; and
         performing a processor-level operation using the correction and the previous record entry as inputs; and
      after the previous valid block is validly stored within the blockchain and after applying the particular consensus operating procedure, generating a corrective indicator including:
         a reference to the previous accumulated value and the previous valid block, and the corrected accumulated value;
      generating a preceding hash value using content of an immediately preceding block in the blockchain;
      generating a corrective block for the blockchain,
         the generating a corrective block for the blockchain responsive to the corrective indicator and the preceding hash value; and
      appending the corrective block to the blockchain,
         the previous valid block remaining valid after the corrective block is appended.

2. A device including:
   a memory configured to store a blockchain; and
   blockchain management circuitry (BMC) in data communication with the memory, the BMC configured to:
      access the blockchain in the memory;
      determine that a previous record entry stored within the blockchain is erroneous;
      after determining that the previous record entry is erroneous, determine a correction for the previous record entry;
      access an identifier of a particular consensus operating procedure;
      select the particular consensus operating procedure from among multiple consensus operating procedures defined within the memory,
         the particular consensus operating procedure selected responsive to the blockchain,
      obtain a previous accumulated value stored within a previous valid block of the blockchain and generated without the correction, the previous valid block being valid based on consistence between the previous valid block and a previous hash stored within the blockchain;
      apply the particular consensus operating procedure to generate a corrected accumulated value from the previous accumulated value, where the BMC is configured to apply the consensus operating procedure by:
         marking the previous record entry as erroneous; and
         performing a processor-level operation using the correction and the previous record entry as inputs;
      after the previous valid block is validly stored within the blockchain and after applying the particular consensus operating procedure, generate a corrective indicator including:
      a reference to the previous accumulated value and the previous valid block; and the corrected accumulated value;
      generate a preceding hash value using content of a immediately preceding block in the blockchain;
      generate a corrective block for the blockchain,
         the corrective block generated responsive to the corrective indicator and the preceding hash value; and
      append the corrective block to the blockchain, the previous valid block remaining valid after the corrective block is appended.

3. A product including:

machine-readable media other than a transitory signal; and instructions stored on the machine-readable media, the instructions configured to, when executed, cause blockchain management circuitry (BMC) to:

determine that a previous record entry stored within a blockchain is erroneous;

after determining that the previous record entry is erroneous, determine a correction for the previous record entry;

access an identifier of a particular consensus operating procedure;

select the particular consensus operating procedure from among multiple consensus operating procedures defined within a memory;

the consensus operating procedure selected responsive to the blockchain;

obtain a previous accumulated value stored within a previous valid block of the blockchain and generated without the correction, the previous valid block being valid based on consistence between the previous valid block and a previous hash stored within the blockchain;

apply the particular consensus operating procedure to generate a corrected accumulated value from the previous accumulated value, where the BMC is configured to apply the consensus operating procedure by:

marking the previous record entry as erroneous; and performing a processor-level operation using the correction and the previous record entry as inputs; and after the previous valid block is validly stored within the blockchain and after applying the particular consensus operating procedure, generate a corrective indicator including:

a reference to the previous accumulated value and the previous valid block, and the corrected accumulated value;

generate a preceding hash value using content of a immediately preceding block in the blockchain;

generate a corrective block for the blockchain, the corrective block generated responsive to the corrective indicator and the preceding hash value; and append the corrective block to the blockchain, the previous valid block remaining valid after the corrective block is appended.

4. The product of claim 3, where the previous record entry is erroneous due to an incorrect timestamp.

5. The product of claim 3, where the previous record entry is erroneous due to an improper classification of a service associated with the previous record entry.

6. The product of claim 3, where previous record entry is erroneous due to a update to the consensus operating procedure causing a range of affected dates.

7. The product of claim 3, where the instructions are further configured to cause the BMC receive a message identifying that the previous record entry is erroneous.

8. The product of claim 7, where the instructions are configured to cause the BMC to receive the message from node circuitry authorized by the BMC.

9. The product of claim 8, where the instructions are configured cause the BMC to authorize the node circuitry responsive to a credential provided by the node circuitry.

10. The product of claim 3, where the previous record entry is erroneous due to latency in transaction reporting.

11. The method of claim 1, where the previous record entry is erroneous due to an incorrect timestamp.

12. The method of claim 1, where the previous record entry is erroneous due to an improper classification of a service associated with the previous record entry.

13. The method of claim 1, where previous record entry is erroneous due to a update to the consensus operating procedure causing a range of affected dates.

14. The method of claim 1, further comprising receiving a message identifying that the previous record entry is erroneous.

15. The method of claim 14, where the receiving the message comprises receiving the message from node circuitry authorized by the BMC.

16. The method of claim 15, further comprising authorizing, via the BMC, the node circuitry responsive to a credential provided by the node circuitry.

17. The method of claim 1, where the previous record entry is erroneous due to latency in transaction reporting.

18. The device of claim 2, where the BMC is further configured to receive a message identifying that the previous record entry is erroneous.

19. The device of claim 18, where the BMC is configured to receive the message from node circuitry authorized by the BMC.

20. The device of claim 19, where the BMC is configured to authorize the node circuitry responsive to a credential provided by the node circuitry.

* * * * *

UNITED STATES PATENT AND TRADEMARK OFFICE
CERTIFICATE OF CORRECTION

PATENT NO. : 10,298,405 B2
APPLICATION NO. : 16/000028
DATED : May 21, 2019
INVENTOR(S) : Noel Vivek Ramathal et al.

Page 1 of 2

It is certified that error appears in the above-identified patent and that said Letters Patent is hereby corrected as shown below:

In the Specification

In Column 13, table 5, Line 23, in the table title, delete "5" and insert in it's place --6--.

In Column 14, Line 3, insert a --(-- prior to "602)".

In Column 14, Line 3, insert a --(-- prior to "604)".

In Column 14, Line 15, insert a --(-- prior to "702)".

In Column 14, Line 16, insert a --(-- prior to "704)".

In Column 14, Line 26, insert a --(-- prior to "802)".

In Column 14, Line 27, insert a --(-- prior to "804)".

In Column 14, Line 38, insert a --(-- prior to "902)".

In Column 14, Line 39, insert a --(-- prior to "904)".

In Column 14, Line 43, insert a --(-- prior to "910)".

In Column 14, Line 52, insert a --(-- prior to "1002)".

In Column 14, Line 53, insert a --(-- prior to "1004)".

In Column 14, Line 65, insert a --(-- prior to "1102)".

In Column 14, Line 66, insert a --(-- prior to "1104)".

Signed and Sealed this
Twenty-first Day of April, 2020

Andrei Iancu
*Director of the United States Patent and Trademark Office*

In Column 15, Line 13, insert a --(-- prior to "1202)".

In Column 15, Line 14, insert a --(-- prior to "1204)".